United States Patent [19]

Beaton

[11] 4,257,949

[45] Mar. 24, 1981

[54] BISNORALDEHYDE-22-ENAMINE PROCESS

[75] Inventor: John M. Beaton, Portage, Mich.

[73] Assignee: The Upjohn Company, Kalamazoo, Mich.

[21] Appl. No.: 87,420

[22] Filed: Oct. 22, 1979

[51] Int. Cl.³ .............................................. C07J 43/00
[52] U.S. Cl. .......................... 260/239.55 R; 260/239.5
[58] Field of Search ...................................... 260/239.5

[56] References Cited

U.S. PATENT DOCUMENTS 2,752,368   1/1956   Holysz ............................... 260/397.3

*Primary Examiner*—Elbert L. Roberts
*Attorney, Agent, or Firm*—Bruce Stein

[57] ABSTRACT

A process which produces bisnoraldehyde-22-enamines in high yield and sufficiently high purity for copper-catalyzed oxygenation by the process of U.S. Pat. No. 3,661,942 has been developed.

60 Claims, No Drawings

BISNORALDEHYDE-22-ENAMINE PROCESS

DESCRIPTION

BACKGROUND OF THE INVENTION

U.S. Pat. Nos. 2,781,342, 3,444,160 and 3,655,649 all disclose processes for producing enamines of 3-keto or $\Delta^4$-3-ketosteroids by use of secondary amines including piperidine and morpholine.

U.S. Pat. No. 3,192,201 claims the 3,22-dienamine (piperidine) of "pyro" bisnoraldehyde. Example 2A discloses "pyro" bisnoraldehyde-22-piperidine enamine.

U.S. Pat. No. 2,752,368 and M. E. Herr and F. W. Heyl in J. Am. Chem. Soc. 74, 3627 (1952) disclose processes to prepare the piperidine and morpholine 22-enamines of bisnoraldehyde. Both items disclose the reaction of bisnoraldehyde and an excess of piperidine in benzene under reflux accompanied by azeotropic removal of water to give the desired bisnoraldehyde-22-enamine product. The morpholine analog was prepared in the same way using an excess of morpholine in toluene.

In the above references the ketone or aldehyde is reacted with an amine to produce the desired enamine with expected splitting out of water. In order to drive the equilibrium in the desired direction the water is removed in the usual manner by azeotropic distillation leaving the desired product. The process of the present invention does not necessitate or require the removal of the water because the process of enamine exchange does not produce water and the product precipitates out and can be recovered in very high purity.

Acid catalysts were disclosed in U.S. Pat. Nos. 2,781,342 and 3,444,160 and inert solvents (substituted amides) were disclosed in U.S. Pat. No. 3,444,160.

U.S. Pat. No. 3,661,942 issued in 1972 claiming a very simple process of oxidative cleavage of an enamine (bisnoraldehyde-22-enamine) to a ketone (progesterone) by use of oxygen and a copper catalyst. In particular, see claim 4. However, in order to take advantage of this copper catalyzed oxidative cleavage the enamine starting material must be quite pure. The prior art processes, cited above, for production of bisnoraldehyde-22-enamine (III) do not in a simple manner produce material of sufficient purity in high yield to be able to utilize directly and efficiently the process of U.S. Pat. No. 3,661,942. The bisnoraldehyde-22-enamine (III) produced by the process of the present invention is sufficiently pure to permit use of the process of U.S. Pat. No. 3,661,942 to convert it to progesterone.

SUMMARY OF THE INVENTION

Disclosed in a process for the preparation of bisnoraldehyde-22-enamine of the formula:

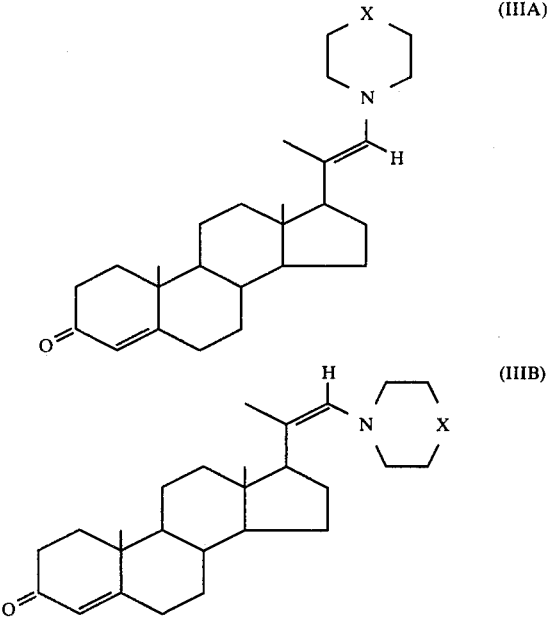

which comprises contacting bisnoraldehyde (I) with an enamine of the formula:

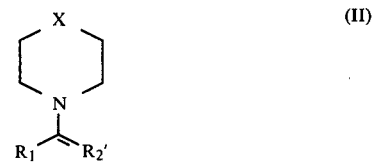

in an organic solvent and recovering the bisnoraldehyde-22-enamine (III).

The process is an improved process for the preparation of bisnoraldehyde-22-enamine (III) from bisnoraldehyde (I) where the improvement comprises contacting bisnoraldehyde (I) with an enamine of formula (II) in an organic solvent and recovering the bisnoraldehyde-22-enamine (III).

Also disclosed is a process for the preparation of bisnoraldehyde-22-enamine (IIIA) which comprises contacting bisnoraldehyde (I) with an enamine of formula (II) in an organic solvent and recovering the bisnoraldehyde-22-enamine (IIIA).

Further disclosed in a process for the preparation of bisnoraldehyde-22-enamine (IIIB) which comprises contacting bisnoraldehyde (I) with an enamine of formula (II) in an organic solvent and recovering the bisnoraldehyde-22-enamine (IIIB).

DETAILED DESCRIPTION OF THE INVENTION

The process of the present invention is set forth in Chart A.

CHART A

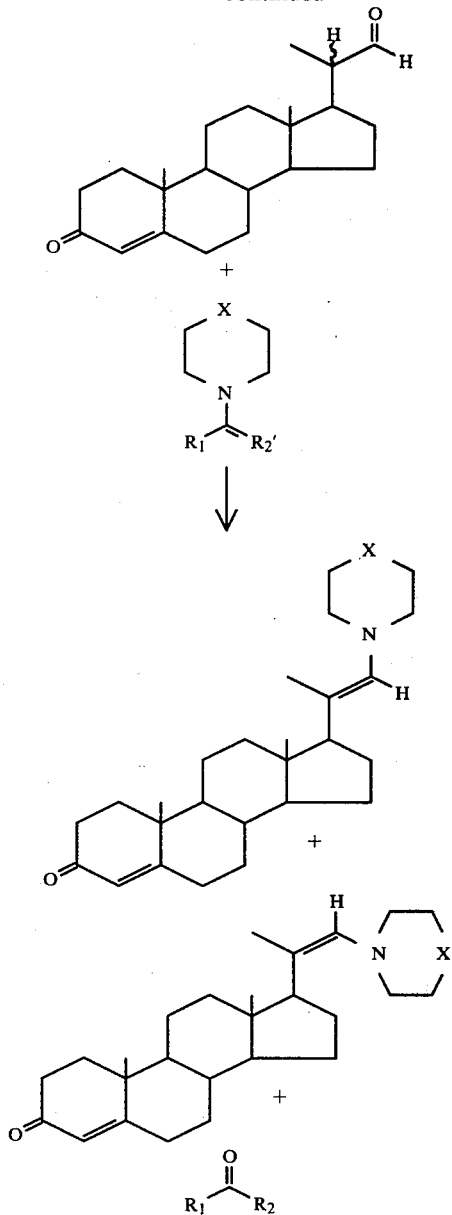

Bisnoraldehyde (I) refers to 3-oxo-23,24-dinorchol-4-en-22-al. Because of the asymmetric center at C-20 bisnoraldehyde as designated by formula (I) includes both epimers. In the process of the present invention, both epimers react similarly and therefore when used the term bisnoraldehyde (I) refers to and includes both epimers.

Bisnoraldehyde (I) and the enamine (II) are mixed in an organic solvent. Virtually any organic solvent is satisfactory. Preferred are halogenated hydrocarbon solvents and polar organic solvents. It is preferred that the halogenated hydrocarbon solvent is selected from the group consisting of chloroform, methylene chloride and ethylene dichloride or mixtures thereof. It is preferred that the polar organic solvent is selected from the group consisting of DMF, methanol, ethanol, isopropanol, t-butanol, THF, acetonitrile, dimethylacetamide, ethylacetate and butyl acetate or mixtures thereof. It is more preferred that the polar organic solvent is selected from the group consisting of DMF, methanol, isopropanol, t-butanol or mixtures thereof. It is most preferred that the polar organic solvent is DMF.

The enamine (II) should be present in the range of 1.0–2.0 equivalents/equivalent of bisnoraldehyde (I). It is more preferred that the enamine (II) should be present in the range of 1.0–1.5 equivalents/equivalent of bisnoraldehyde (I). It is preferred that the enamine (II) be either cyclohexanone piperidine enamine or cyclohexanone morpholine enamine. It is most preferred that the cyclohexanone enamine (II) be the cyclohexanone piperidine enamine (II).

The bisnoraldehyde (I) and the enamine (II) are contacted under an inert atmosphere such as nitrogen. The reaction proceeds adequately at room temperature, especially when an acid catalyst is present. The mixture may be warmed to a temperature less than the solvent's boiling point but that it not necessary.

While the reaction proceeds in the absence of a catalyst the reaction rate is quite slow. To obtain reasonable reaction rates at convenient temperatures (room temperature) an acid catalyst is used. The particular acid and the quantity are not critical. It is preferred that the acid catalyst be selected from the group consisting of acetic, p-TSA, methanesulfonic, phosphoric, propionic and oxalic. It is more preferred that the acid be either acetic or p-TSA.

The progress of the reaction is monitored (TLC or GLC) and when complete, about 1 to about 48 hours, the reaction mixture is cooled (−50° to 0°) with stirring and then the bisnoraldehyde-22-enamine (III) is recovered by filtration. The crystals are washed with cold solvent to remove impurities and may be used as such in subsequent air oxidation, or dried in the usual manner. Additional bisnoraldehyde enamine (III) or bisnoraldehyde (I) itself can be recovered from the combined filtrate-wash mixture by procedures well known to those skilled in the art, see Examples 1 and 3.

The bisnoraldehyde-22-enamine (III) obtained by the process of the present invention exists in 2 different isomeric forms, trans or E (IIIA) and cis or Z (IIIB). When the term bisnoraldehyde-22-enamine (III) is used it refers to and includes either or both isomers (IIIA and IIIB). While in theory both trans (IIIA) and cis (IIIB) isomers would be produced by the process of the present invention, in practice it appears that one isomer, probably trans (IIIA) is either solely produced or produced in a substantially larger (90–99%) amount than the other isomer, probably cis (IIIB). However, it is not critical as to whether one or both isomers are produced by the process of the present invention because either isomer (IIIA and/or IIIB) would be transformed by the copper catalyzed oxygenation process of U.S. Pat. No. 3,661,942, to progesterone.

The process of the present invention has an advantage over other known methods to produce the bisnoraldehyde-22-enamine (III) in that removal of water from the reaction mixture is not required since water is not formed. This permits use of a wide variety of organic solvents and permits the selection of a solvent in which the desired bisnoraldehyde-22-enamine (III) is relatively insoluble. Bisnoraldehyde-22-enamine (III) is obtained in high yield (89–93% chemical) and in very high purity (>99%) by simple filtration.

The definitions and explanations below are for the terms as used throughout the entire patent application including both the specification and claims.

All temperatures are in degrees Centigrade.

TLC refers to thin-layer chromatography.
GLC refers to gas-liquid chromatography.
THF refers to tetrahydrofuran.
DMF refers to dimethylformamide.
p-TSA refers to p-toluenesulfonic acid.
X is an oxygen atom, methylene (—CH$_2$—) or ethylene (—CH$_2$CH$_2$—) group.
Bisnoraldehyde refers to 3-oxo-23,24-dinorchol-4-en-22-al (both isomers)

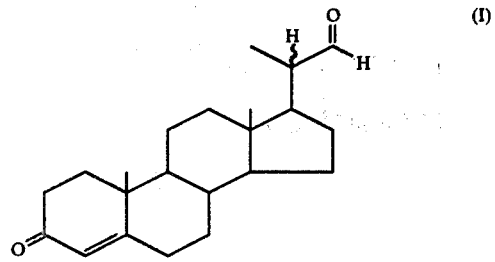

also known as 23,24-dinorchol-4-en-3-on-22-al or as 3-ketobisnor-4-cholen-22-al (U.S. Pat. No. 3,661,942, Example 1).

Bisnoraldehyde-22-enamine refers to either or both isomers (IIIA and/or IIIB).

R$_1$ is a hydrogen atom, or alkyl group of 1 through 5 carbon atoms.

R$_2$ is an alkyl group of 1 through 5 carbon atoms with the proviso that when R$_1$ is not a hydrogen atom, R$_1$ and R$_2$ together with the attached carbon atom can be cycloalkyl of 5 through 8 carbon atoms.

R$_2'$ is an alkylidene group of 1 through 5 carbon atoms with the proviso that when R$_1$ is not a hydrogen atom, R$_1$ and R$_2'$ together with the attached carbon atom can be cycloalkylidene of 5 through 8 carbon atoms.

EXAMPLES

Without further elaboration, it is believed that one skilled in the art can, using the preceding description, practice the present invention to its fullest extent. The following preferred specific embodiments are, therefore, to be construed as merely illustrative, and not limiting of the preceding disclosure in any way whatsoever.

Preparation 1

Cyclohexanone Piperidine Enamine (II)

Piperidine (570 ml.), cyclohexanone (570 ml.), hexane (570 ml.) and acetic acid (1.0 ml.) are refluxed with a Dean-Stark trap under nitrogen for 21 hours during which time the lower phase (about 100 ml.) is removed from the trap. The mixture is heated to 90°–100° under vacuum increasing the vacuum to 29 inches until distillation ceases giving the title compound as an oily residue.

Preparation 2

Cyclohexanone morpholine enamine (II)

A mixture of morpholine (697 ml.), cyclohexanone (820 ml.) and hexane (800 ml.) is heated to reflux under nitrogen with a Dean-Stark trap for 18 hours. The aqueous phase (206 ml.) is collected in the distillate trap. The mixture is distilled under vacuum increasing the vacuum to 29 inches and 90°–100° to give the title compound as an oily residue.

EXAMPLE 1

Bisnoraldehyde Piperidine Enamine (III)

Bisnoraldehyde (230.5 g.), DMF (351 ml.), cyclohexanone piperidine enamine (II, Preparation 1, 156 ml.) and acetic acid (1.8 ml.) are stirred under nitrogen at 30°–31° for 21 hours. The mixture is cooled to −5°, stirred for 10 minutes and filtered. The solids are washed with cold methanol (about 500 ml.), dried under vacuum at 60° to give the title compound, 257.9 g (92.2% chemical yield) which by GLC is found to contain 99.3% 22-monoenamine and no 3,22-bisenamine.

The filtrates are pooled, the methanol is distilled off, and the remaining solution stirred overnight with water (50 ml.) and acetic acid (5 ml.). Water (850 ml.) is added and the solids separated by decantation, extracted into methylene chloride and crystallized by displacement with hexane. The crystals are obtained by filtration and recycled through the exchange reaction on a small scale to give additional title compound, 10.9 g (3.9% chemical yeild) of 99.3% purity as determined by GLC.

EXAMPLE 2

Bisnoraldehyde Morpholine Enamine (III)

Bisnoraldehyde (230.5 g.), DMF (351 ml.), cyclohexanone morpholine enamine (II, Preparation 2, 176 ml.) and acetic acid (1.8 ml.) are stirred at 30° for 15 hours. The mixture is cooled and filtered. The solids are washed as described in Example 1 and dried to give the title compound 240.5 g (86.2% chemical yield) which by GLC is found to contain 99.1% enamine.

No salvage from the mother liquors was attempted.

EXAMPLE 3

Bisnoraldehyde Morpholine Enamine (III)

Bisnoraldehyde (65.7 g.), isopropanol (100 ml.), cyclohexanone morpholine enamine (Preparation 2, 87.1%, 49.6 ml.) and acetic acid (0.5 ml.) are stirred at 20°–25° for 105 minutes. Isopropanol (100 ml.) is added and stirring is continued. After 17 hours the mixture is cooled, filtered, the solids washed well with isopropanol and dried to give the title compound 69.2 g (87.0% chemical yield) which by GLC is found to contain 99.0% enamine.

The isopropanol filtrate and washes are diluted with water and refiltered to give a second crop (2.7 g) which by GLC assay shows 93.1% enamine.

I claim:

1. A process for the preparation of bisnoraldehyde-22-enamines of the formula:

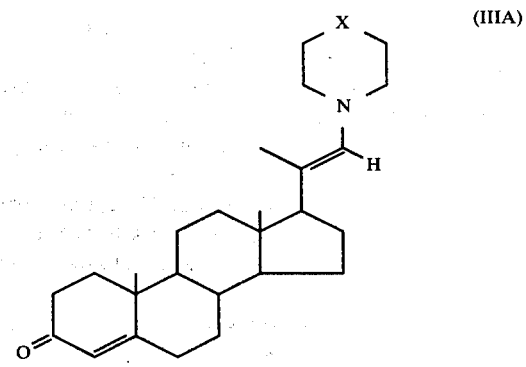

-continued

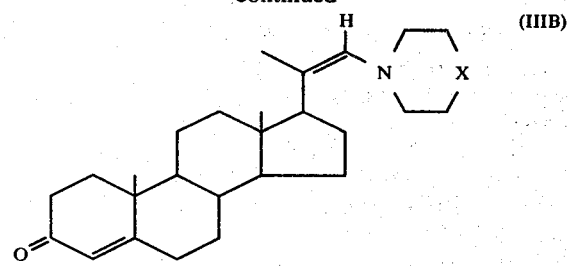

which comprises
(a) contacting bisnoraldehyde (I) with an enamine of the formula:

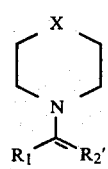

in an organic solvent and
(b) recovering the bisnoraldehyde-22-enamine (III) where X, $R_1$ and $R_2'$ are defined in the specification.

2. A process according to claim 1 where the organic solvent is a polar organic solvent.

3. A process according to claim 2 where the polar organic solvent is selected from the group consisting of DMF, methanol, ethanol, isopropanol, t-butanol, THF, acetonitrile, dimethylacetamide, ethyl acetate and butyl acetate or mixtures thereof.

4. A process according to claim 3 where the polar organic solvent is selected from the group consisting of DMF, methanol, isopropanol, t-butanol and THF.

5. A process according to claim 4 where the polar organic solvent is DMF.

6. A process according to claim 1 where the enamine (II) is cyclohexanone piperidine enamine.

7. A process according to claim 1 where the enamine (II) is cyclohexanone morpholine enamine.

8. A process according to claim 1 where the enamine (II) is present in the range of 1.0–2.0 equivalents/equivalent of bisnoraldehyde (I).

9. A process according to claim 8 where the enamine (II) is present in the range of 1.0–1.5 equivalents/equivalent of bisnoraldehyde (I).

10. A process according to claim 1 which is catalyzed by a catalytic amount of an acid.

11. A process according to claim 1 which is catalyzed by a catalytic amount of acetic acid or p-TSA.

12. A process according to claim 1 where the organic solvent is a halogenated hydrocarbon.

13. A process according to claim 12 where the halogenated hydrocarbon solvent is selected from the group consisting of chloroform, methylene chloride or ethylene dichloride or mixtures thereof.

14. A process for the preparation of bisnoraldehyde-22-enamines of the formula:

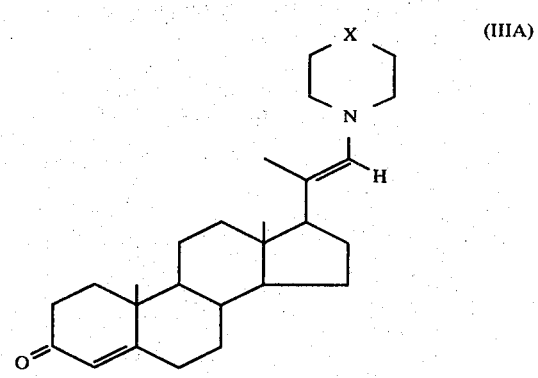

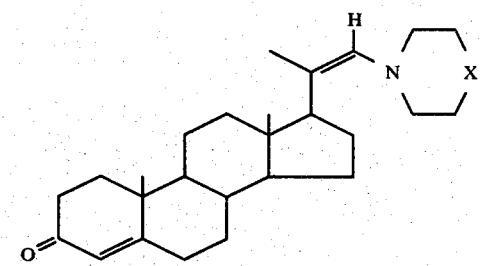

which comprises
(a) contacting bisnoraldehyde (I) with 1.0–1.5 equivalents of cyclohexanone piperidine enamine (II) or cyclohexanone morpholine enamine (II) in DMF and
(b) recovering the bisnoraldehyde-22-enamine (III) where X is defined in the specification.

15. A process according to claim 14 which is catalyzed by a catalytic amount of acetic acid or p-TSA.

16. An improved process for the preparation of bisnoraldehyde-22-enamines of the formula:

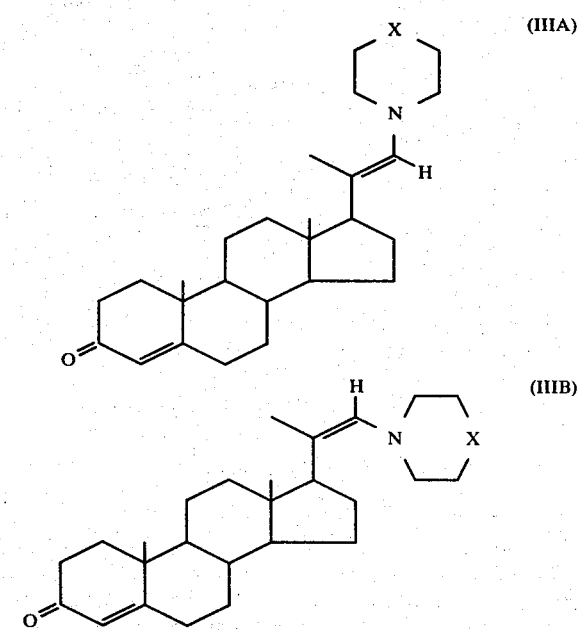

where the improvement comprises contacting bisnoraldehyde (I) with an enamine of the formula:

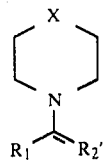

(II)

in an organic solvent and recovering the bisnoraldehyde-22-enamine (III) where X, $R_1$ and $R_2'$ are defined in the specification.

17. An improved process according to claim 16 where the organic solvent is a polar organic solvent.

18. An improved process according to claim 17 where the polar organic solvent is selected from the group consisting of DMF, methanol, ethanol, isopropanol, t-butanol, THF, acetonitrile, dimethylacetamide, ethyl acetate and butyl acetate or mixtures thereof.

19. An improved process according to claim 18 where the polar organic solvent is selected from the group consisting of DMF, methanol, isopropanol, t-butanol and THF.

20. An improved process according to claim 19 where the polar organic solvent is DMF.

21. An improved process according to claim 16 where the enamine (II) is cyclohexanone piperidine enamine.

22. An improved process according to claim 16 where the enamine (II) is cyclohexanone morpholine enamine.

23. An improved process according to claim 16 where the enamine (II) is present in the range of 1.0–2.0 equivalents/equivalent of bisnoraldehyde (I).

24. An improved process according to claim 23 where the enamine (II) is present in the range of 1.0–1.5 equivalents/equivalent of bisnoraldehyde (I).

25. An improved process according to claim 16 which is catalyzed by a catalytic amount of an acid.

26. An improved process according to claim 16 which is catalyzed by a catalytic amount of acetic acid or p-TSA.

27. An improved process according to claim 16 where the organic solvent is a halogenated hydrocarbon.

28. An improved process according to claim 27 where the organic solvent is selected from the group consisting of chloroform, methylene chloride or ethylene dichloride or mixtures thereof.

29. An improved process for the preparation of bisnoraldehyde-22-enamine of the formula:

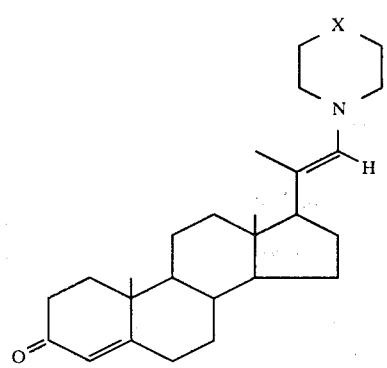

(IIIA)

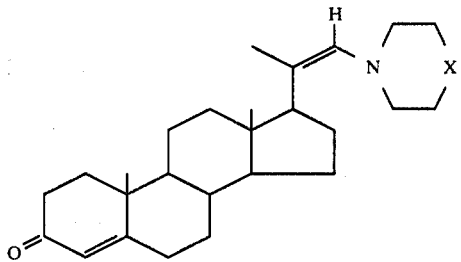

(IIIB)

which comprises contacting bisnoraldehyde (I) with 1.0–1.5 equivalents of cyclohexanone piperidine enamine (II) or cyclohexanone morpholine enamine (II) in DMF and recovering the bisnoraldehyde-22-enamine (III) where X is defined in the specification.

30. An improved process according to claim 29 which is catalyzed by a catalytic amount of acetic acid or p-TSA.

31. A process for the preparation of bisnoraldehyde-22-enamine of the formula:

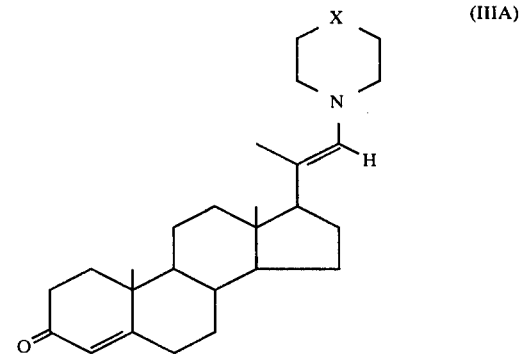

(IIIA)

which comprises
(a) contacting bisnoraldehyde (I) with an enamine of the formula:

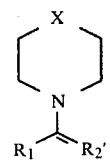

(II)

in an organic solvent and
(b) recovering the bisnoraldehyde-22-enamine (IIIA) where X, $R_1$ and $R_2'$ are defined in the specification.

32. A process according to claim 31 where the organic solvent is a polar organic solvent.

33. A process according to claim 32 where the polar organic solvent is selected from the group consisting of DMF, methanol, ethanol, isopropanol, t-butanol, THF, acetonitrile, dimethylacetamide, ethyl acetate and butyl acetate or mixtures thereof.

34. A process according to claim 33 where the polar organic solvent is selected from the group consisting of DMF, methanol, isopropanol, t-butanol and THF.

35. A process according to claim 34 where the polar organic solvent is DMF.

36. A process according to claim 31 where the enamine (II) is cyclohexanone piperidine enamine.

37. A process according to claim 31 where the enamine (II) is cyclohexanone morpholine enamine.

38. A process according to claim 31 where the enamine (II) is present in the range of 1.0-2.0 equivalents/equivalent of bisnoraldehyde (I).

39. A process according to claim 38 where the enamine (II) is present in the range of 1.0-1.5 equivalents/equivalent of bisnoraldehyde (I).

40. A process according to claim 31 which is catalyzed by a catalytic amount of an acid.

41. A process according to claim 31 which is catalyzed by a catalytic amount of acetic acid or p-TSA.

42. A process according to claim 31 where the organic solvent is a halogenated hydrocarbon.

43. A process according to claim 42 where the halogenated hydrocarbon solvent is selected from the group consisting of chloroform, methylene chloride or ethylene dichloride or mixtures thereof.

44. A process for the preparation of bisnoraldehyde-22-enamine of the formula:

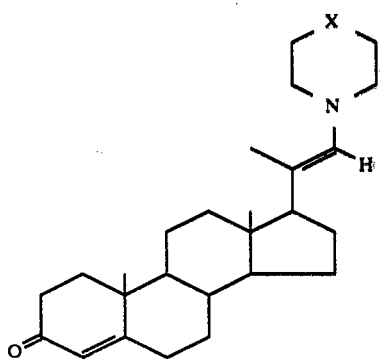

(IIIA)

which comprises
(a) contacting bisnoraldehyde (I) with 1.0-1.5 equivalents of cyclohexanone piperidine enamine (II) or cyclohexanone morpholine enamine (II) in DMF and
(b) recovering the bisnoraldehyde-22-enamine (IIIA) where X is defined in the specification.

45. A process according to claim 44 which is catalyzed by a catalytic amount of acetic acid or p-TSA.

46. A process for the preparation of bisnoraldehyde-22-enamine of the formula:

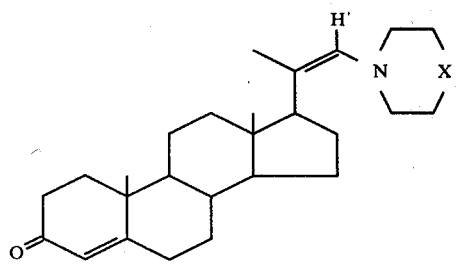

(IIIB)

which comprises
(a) contacting bisnoraldehyde (I) with an enamine of the formula:

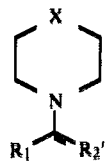

(II)

in an organic solvent and
(b) recovering the bisnoraldehyde-22-enamine (IIIB) where X, $R_1$ and $R_2'$ are defined in the specification.

47. A process according to claim 46 where the organic solvent is a polar organic solvent.

48. A process according to claim 47 where the polar organic solvent is selected from the group consisting of DMF, methanol, ethanol, isopropanol, t-butanol, THF, acetonitrile, dimethylacetamide, ethyl acetate and butyl acetate or mixtures thereof.

49. A process according to claim 48 where the polar organic solvent is selected from the group consisting of DMF, methanol, isopropanol, t-butanol and THF.

50. A process according to claim 49 where the polar organic solvent is DMF.

51. A process according to claim 46 where the enamine (II) is cyclohexanone piperidine enamine.

52. A process according to claim 46 where the enamine (II) is cyclohexanone morpholine enamine.

53. A process according to claim 46 where the enamine (II) is present in the range of 1.0-2.0 equivalents/equivalent of bisnoraldehyde (I).

54. A process according to claim 53 where the enamine (II) is present in the range of 1.0-1.5 equivalents/equivalent of bisnoraldehyde (I).

55. A process according to claim 46 which is catalyzed by a catalytic amount of an acid.

56. A process according to claim 46 which is catalyzed by a catalytic amount of acetic acid or p-TSA.

57. A process according to claim 46 where the organic solvent is a halogenated hydrocarbon.

58. A process according to claim 57 where the halogenated hydrocarbon solvent is selected from the group consisting of chloroform, methylene chloride or ethylene dichloride or mixtures thereof.

59. A process for the preparation of bisnoraldehyde-22-enamine of the formula:

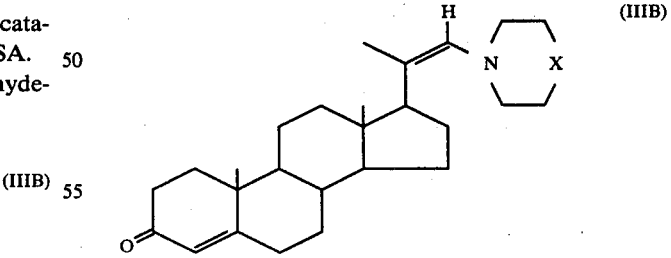

(IIIB)

which comprises
(a) contacting bisnoraldehyde (I) with 1.0-1.5 equivalents of cyclohexanone piperidine enamine (II) or cyclohexanone morpholine enamine (II) in DMF and
(b) recovering the bisnoraldehyde-22-enamine (IIIB) where X is defined in the specification.

60. A process according to claim 59 which is catalyzed by a catalytic amount of acetic acid or p-TSA.

* * * * *